US00PP17687P2

(12) United States Plant Patent
Carruth

(10) Patent No.: US PP17,687 P2
(45) Date of Patent: May 1, 2007

(54) CLIMBING ROSE PLANT NAMED 'WEKAMRAV'

(50) Latin Name: *Rosa hybrida*
Varietal Denomination: WEKamrav

(75) Inventor: Thomas F. Carruth, Altadena, CA (US)

(73) Assignee: Weeks Wholesale Rose Grower, Inc., Upland, CA (US)

( * ) Notice: Subject to any disclaimer, the term of this patent is extended or adjusted under 35 U.S.C. 154(b) by 0 days.

(21) Appl. No.: 11/281,289

(22) Filed: Nov. 17, 2005

(51) Int. Cl.
*A01H 5/00* (2006.01)

(52) U.S. Cl. ..... Plt./115

(58) Field of Classification Search ..... Plt./115
See application file for complete search history.

(56) References Cited

U.S. PATENT DOCUMENTS

PP7,718 P 11/1991 Meilland
PP9,211 P 7/1995 Fryer

*Primary Examiner*—Kent Bell
(74) *Attorney, Agent, or Firm*—McKee, Voorhees & Sease, P.L.C.

(57) ABSTRACT

A new variety of Climbing rose suitable for garden decoration, having flowers of deep velvet red coloration.

1 Drawing Sheet

Classification: The present invention relates to a new *Rosa hybrida* plant.

Variety denomination: The new plant has the varietal denomination 'WEKamrav'.

BACKGROUND OF THE INVENTION

This invention relates to a new and distinct variety of Climbing Rose. It has as its seed parent the variety known as 'MEIcauf' (U.S. Plant Pat. No. 7,718) and as its pollen parent the variety known as 'FRYtrooper' (U.S. Plant Pat. No. 9,211).

SUMMARY OF THE INVENTION

Among the features which distinguish the new variety from other presently available and commercial rose cultivars known to the inventor are the following combination of characteristics: its even deep velvet red coloration that last throughout the life of the flower, its conspicuous neck, its red suffusion on the petiolule and its numerous stipitate glands on the stipules of the new shoots. The plant has a spreading climbing growing habit, suitable for outdoor garden decoration.

Asexual reproduction of the new variety by budding as performed in Kern County and Upland, Calif., shows that the foregoing and other distinguishing characteristics come true to form and are established and transmitted through succeeding asexual propagations. 'WEKamrav' may be asexually propagated by cuttings, budding and grafting. The budding and grafting successfully occurred on the plant/rootstock *Rosa hybrida* cv. 'Dr. Huey'.

COMPARISON WITH PARENTS

The new rose may be distinguished from its seed parent, 'MEIcauf' by the following combination of characteristics: whereas 'WEKamrav' bears medium sized flowers (about 4.8 to about 7.2 cm. in diameter) of deep velvet red coloration, 'MEIcauf' bears significantly larger flowers (about 13.0 to about 14.0 cm. in diameter) of turkey red coloration. The new variety is classified as a climbing rose with a spreading climbing growing habit, whereas the seed parent is classified as a hybrid tea rose with an erect and upright significantly shorter growing habit.

The new variety may be distinguished from its pollen parent, 'FRYtrooper' by the following combination of characteristics: whereas 'WEKamrav' bears flowers of deep velvet red coloration with double petalage (about 25 to 36 petals), 'FRYtrooper' bears flowers of clear red coloration with significantly lesser petalage (about 18 to 22 petals). The new variety is classified as a climbing rose with a spreading climbing growing habit, whereas the pollen parent is classified as a shrub rose with a bushy, compact and upright significantly shorter growing habit.

COMPARISON WITH THE CLOSEST COMMERCIALLY AVAILABLE CULTIVAR

The new variety may be distinguished from its closest commercially available cultivar, 'WEKsamsou' by the following combination of characteristics: whereas 'WEKamrav' bears flowers of deep velvet red coloration with double petalage (about 25 to 36 petals), 'WEKsamsou' bears flowers of medium cherry red coloration with significantly heavier petalage (about 36 to 50 petals). The new variety bears moderately small foliage (about 7.4 to about 11.9 cm. in length and about 5.2 to about 8.1 cm. in width), whereas the closest commercially available cultivar bears significantly larger foliage (about 7.2 to about 13.3 cm. in length and about 7.0 to about 10.2 cm. in width). 'WEKamrav' has a spreading climbing medium height growing habit with climbing canes about 150 to about 250 cm. in length, whereas 'WEKsamsou' has a spreading growth habit with significantly longer climbing canes of about 250 to about 380 cm. in length.

BRIEF DESCRIPTION OF ILLUSTRATION

The accompanying photograph illustrates the new variety and shows the flowering thereof from bud to full bloom depicted in color as nearly correct as it is possible to make in a color illustration of the character. Throughout this specification, color references and/or values are based upon the Colour Chart of The Royal Horticultural Society of London, England (1966), except where common terms of color definition are employed.

DESCRIPTION OF THE NEW VARIETY

The following description is of 3 to 4 year-old rose plants of the new variety grown outdoors in Upland, Calif. in the month of October. Phenotypic expression may vary with environmental, cultural and climatic conditions, as well as differences in conditions of light and soil.

BOTANICAL DESIGNATION

The new variety botanical designation is *Rosa hybrida* 'WEKamrav'.

FLOWER

The new variety sometimes bears its flowers singly, sometimes in clusters of two to six or more per stem. Flowers may be borne in regular rounded clusters on strong medium length to long stems (about 38 to about 100 cm.). Outdoors, the plant blooms abundantly and nearly continuously during the growing season. The flowers have a very slight tea fragrance.

BUD

The peduncle is about 2.4 to about 5.8 cm. in length, of somewhat slender caliper (about 0.2 to about 0.3 cm. in diameter), and usually erect. It is moderately smooth, with some stipitate glands and few hairs. Peduncle color is between 144A and 146B often heavily suffused, especially on the side exposed to the sun, with between 183A and 187B.

Before the calyx breaks, the bud is about 0.9 to about 1.4 cm. in diameter at the widest point, about 1.1 to about 1.8 cm. in length, and pointed to somewhat ovoid in shape with a conspicuous neck. The surface of the bud bears some foliaceous appendages and some stipitate glands and hairs, usually with slender entire foliaceous parts extending beyond the tip of the bud about ¼ or more of its length. Bud color is between 144A and 146A often heavily suffused, especially on the side exposed to the sun, with between 183A and 187B.

The sepals are about 1.3 to about 2.5 cm. in length and about 0.5 to about 0.8 cm. in width at the widest point. The outer surface color of the sepal is between 144A and 146A often heavily suffused, especially on the side exposed to the sun, with between 183A and 187B. The inner surface color of the sepal is between 137A and 139D and covered with fine wooly tomentum; sepal margins are lined with few stipitate glands and numerous hairs.

The receptacle of the flower is of very long length (about 0.6 to about 1.1 cm.) and average in caliper (about 0.6 to about 0.8 cm. in diameter). The receptacle is moderately oblong to somewhat ovoid in form. Its surface is very smooth with some hairs and with thick fleshy walls. The receptacle color is between 144A and 146A sometimes moderately suffused, especially on the side exposed to the sun, with between 183A and 187B.

As the petals open (after the calyx breaks), the bud is about 1.5 to about 2.2 cm. in diameter at the widest point, about 1.5 to about 2.6 cm. in length, and moderately ovoid in form. The color of the under surfaces of the newly opened petals is between 187B and 53A. At the point where the petal attaches, there is a very small zone of between 5C and 4B. The color of the upper surfaces of the newly opened petals is between 53A and 46A. At the point where the petal attaches, there is a small zone of between 13A and 14B.

BLOOM

When fully open, the bloom ranges from about 4.8 to about 7.2 cm. in diameter. Petalage is double with about 25 to 36 petals and about 4 to 10 petaloids irregularly arranged. When partially open, the bloom form is cupped to globular and the petals are moderately tightly spiraled to cupped with petal edges somewhat reflexed outward. When fully open, the bloom form is cupped and the petals are loosely cupped with petal edges somewhat reflexed outward.

PETALS

The substance of the petals is moderately heavy and of medium thickness, with upper surfaces moderately velvety and under surfaces very shiny. The petals are about 1.5 to about 3.5 cm. in length and about 1.0 to about 3.7 cm. in width at the widest point. Petal margins are entire.

The outer petals are moderately rounded to somewhat obovate in shape with mostly mucronate and sometimes rounded apices.

The inner petals are obovate in shape with mostly mucronate and sometimes rounded apices.

Petaloids are about 0.8 to about 2.6 cm. in length and about 0.5 to about 1.3 cm. in width at the widest point. Petaloids are irregularly shaped somewhat obovate to oblanceolate with rounded apices.

NEWLY OPENED FLOWER

The under surface color of the outer petals is between 53A and 46A. At the point where the petal attaches, there is a very small zone of between 5C and 4B. The upper surface color of the outer petals is between 46A and 45A. At the point where the petal attaches, there is a small zone of between 13C and 14C.

The under surface color of the intermediate and inner petals is lighter than between 53A and 46A. The upper surface color of the intermediate and inner petals is between 46A and 45A.

The under and upper surface color of the petaloids are similar in coloration to the upper and under surfaces of the intermediate and inner petals.

The general tonality of the newly opened flower is between 46A and 45A.

THREE-DAY-OLD FLOWER

The under surface color of the outer petals is between 53A and 46A. At the point where the petal attaches, there is a very small zone of between 5D and 4C. The upper surface color of the outer petals is between 46A and 45B. At the point where the petal attaches, there is a small zone of between 13C and 14C.

The under surface color of the intermediate and inner petals is lighter than between 53A and 46A. The upper surface color of the intermediate and inner petals is between 46A and 45B.

The under and upper surface color of the petaloids are similar in coloration to the upper and under surfaces of the intermediate and inner petals.

The general tonality of the three-day-old flower is between 46A and 45B.

On the spent bloom, the petals usually drop off cleanly.

In October in Upland, Calif., blooms on the bush growing outdoors generally last about four to five days. Cut roses from plants grown outdoors and kept at normal indoor living temperatures generally last about four to five days.

MALE REPRODUCTIVE ORGANS

Stamens are average in number (average about 85) and are arranged regularly about the pistils; a few are mixed with petaloids. The filaments are of moderately short length (about 0.4 to about 0.8 cm.) most with anthers. Filaments are between 12B and 13C in color sometimes lightly suffused with between 33A and 33B. The anthers are moderately small for the class and all open approximately at the same time. Anther color is between 22A and 22C when immature and between 200A and 163C at maturity. Pollen is somewhat abundant and between 20A and 22B in color.

FEMALE REPRODUCTIVE ORGANS

Pistils vary in number (average about 70). The styles are moderately even, short in length (about 0.2 to about 0.5 cm.), somewhat thin in caliper and loosely bunched. Stigma color is between 11C and 12D. Style color is between 2D and 1D usually moderately suffused with between 53A and 53B. Ovaries are usually all enclosed in the calyx.

Hips are of moderately long length (about 1.7 to about 2.3 cm.), globular to almost round in form, and between 34B and 33B in color when ripe. The hip surface is smooth with thick fleshy walls. The sepals are somewhat fugacious and usually straight in shape.

The seeds are irregularly rounded, smooth in texture, approximately 7 to about 15 per hip, about 0.4 to about 0.7 cm. in diameter at the widest point and between 165C and 164C in color.

FOLIAGE

The compound leaves are usually comprised of three to seven leaflets and are borne abundantly. The five-leaflet leaves are about 7.4 to about 11.9 cm. in length and about 5.2 to about 8.1 cm. in width at the widest point, moderately leathery to somewhat crisp in texture and glossy in finish. The terminal leaflets are about 2.6 to about 4.2 cm. in length and about 1.9 to about 2.9 cm. in width at the widest point, shaped ovate to somewhat oval with acute apices and rounded bases. Their margins are usually simply serrate.

The upper surface color of the mature leaf is between 147A and 137A. The under surface color of the mature leaf is between 147B and 146A. The upper surface color of the young leaf is between 146A and 152A, usually heavily suffused with between 183A and 187B. The under surface color of the young leaf is between 147B and 146B, usually heavily suffused with between 187B and 183A.

The rachis is somewhat light in caliper and rough. The upper side is moderately deeply grooved with few hairs and stipitate glands on the edges of the grooves. The under side of the rachis is rough with some hairs and few stipitate glands and small prickles. The rachis color is between 145A and 144A often moderately suffused on the young leaves with between 187A and 187B.

The stipules are about 1.1 to about 1.7 cm. in length and of medium width (about 0.4 to about 0.5 cm.) with moderately long straight points that usually turn out at an angle of more than 45 degrees and often recurve toward the stem. The stipules color is between 146C and 146A often moderately suffused with between 187A and 187B. The stipule margin and under side of the stipule on the new shoots are often lined and covered with numerous stipitate glands.

The petiole is somewhat light in caliper and rough. The upper side is moderately deeply grooved with few hairs and stipitate glands on the edges of the grooves. The under side of the petiole is rough with some hairs and few stipitate glands and small prickles. The petiole is about 0.9 to about 2.2 cm. in length and about 0.1 to about 0.15 cm in diameter at the widest point. The petiole color is between 145A and 144A often moderately suffused on the young leaves with between 187A and 187B. The petiolule is often moderately suffused with between 187A and 187B.

The plant displays an above average degree of resistance to powdery mildew and rust as compared to other commercial varieties grown under comparable conditions in Upland, Calif. The plant's winter hardiness and drought/heat tolerance are yet to be determined.

GROWTH

The plant has a spreading climbing medium height growing habit with climbing canes about 150 to about 250 cm. in length with very full branching. It displays moderately vigorous growth and the canes are of somewhat light caliper for the class.

The color of the major stems is between 146B and 152B. They bear many large prickles that are about 0.7 to about 1.1 cm. in length. The large prickles are almost straight and angled slightly downward with a moderately long somewhat narrow oval base; prickle color is between 201B and 177C. The major stem bears several small prickles of similar shape and coloration.

The color of the branches is between 146B and 146A. They bear many large prickles which are of similar size and shape to the large prickles on the major stems; prickle color is between 173D and 162C often moderately suffused with between 183A and 184B. The branches bear several small prickles of similar shape and coloration.

The color of the new shoots is between 144A and 146A often heavily suffused with between 187B and 183A. They bear many large prickles which are of similar size and shape to the large prickles on the major stems; prickle color is between 187A and 183A. The shoots bear several small prickles of similar shape and coloration.

I claim:

1. A new and distinct Climbing rose plant of the variety substantially as described and illustrated herein.

* * * * *

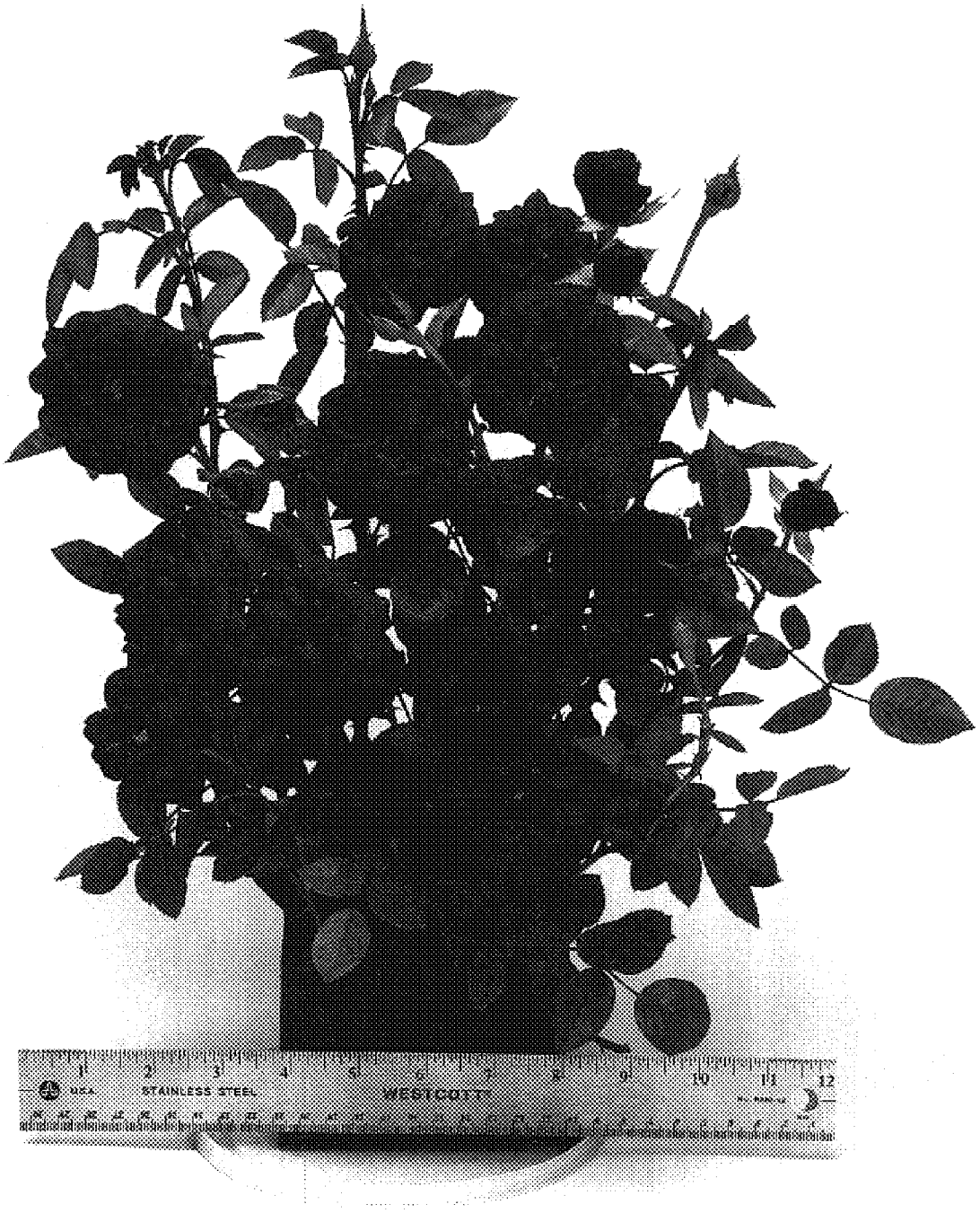
STAINLESS STEEL
WESTCOTT